US006488956B1

(12) United States Patent
Paradissis et al.

(10) Patent No.: US 6,488,956 B1
(45) Date of Patent: Dec. 3, 2002

(54) MULTI-VITAMIN AND MINERAL SUPPLEMENTS FOR WOMEN

(75) Inventors: George N. Paradissis, St. Louis, MO (US); R. Saul Levinson, Chesterfield, MO (US); Robert C. Cuca, Edwardsville, IL (US); Patrick Paul Vanek, Middletown, MO (US)

(73) Assignee: Drugtech Corporation, Wilmington, DE (US)

( * ) Notice: Subject to any disclaimer, the term of this patent is extended or adjusted under 35 U.S.C. 154(b) by 0 days.

(21) Appl. No.: 09/448,744

(22) Filed: Nov. 24, 1999

Related U.S. Application Data

(63) Continuation of application No. 09/128,466, filed on Aug. 4, 1998, now abandoned, which is a continuation-in-part of application No. 08/474,071, filed on Jun. 7, 1995, now Pat. No. 5,869,084, which is a continuation-in-part of application No. 08/262,515, filed on Jun. 20, 1994, now abandoned.

(51) Int. Cl.$^7$ .......................... A61K 47/00; A61K 9/20; A61K 9/28
(52) U.S. Cl. ................. 424/439; 424/474; 424/464
(58) Field of Search .................. 424/474, 439, 424/464

(56) References Cited

U.S. PATENT DOCUMENTS

| | | | | |
|---|---|---|---|---|
| 4,431,634 A | * | 2/1984 | Ellenbogen | 424/147 |
| 4,500,515 A | * | 2/1985 | Libby | 424/154 |
| 4,710,387 A | * | 12/1987 | Uiterwaal et al. | 426/72 |
| 4,752,479 A | | 6/1988 | Briggs et al. | 424/472 |
| 4,994,283 A | | 2/1991 | Mehansho et al. | 426/74 |
| 5,514,382 A | | 5/1996 | Sultenfuss | 424/440 |
| 5,569,459 A | | 10/1996 | Shylankevich | 424/195.1 |
| 5,744,161 A | * | 4/1998 | Majeed et al. | 424/464 |
| 5,776,504 A | * | 7/1998 | McCarty | 424/682 |

FOREIGN PATENT DOCUMENTS

| | | | |
|---|---|---|---|
| WO | WO 95/35098 | 12/1995 | A61K/9/20 |

OTHER PUBLICATIONS

*Physicians' Desk Reference* 1011 (53$^{rd}$ Ed., 1999).
*Physicians' Desk Reference* 1522 (53$^{rd}$ Ed., 1999).
*Physicians' Desk Reference* 1692 (53$^{rd}$ Ed., 1999).
*Physicians' Desk Reference* 2143 (53$^{rd}$ Ed., 1999).
*Physicians' Desk Reference* 2802 (53$^{rd}$ Ed., 1999).
*Physicians' Desk Reference* 2916 (53$^{rd}$ Ed., 1999).
*Physicians' Desk Reference* 2917 (53$^{rd}$ Ed., 1999).
*Physicians' Desk Reference* 3112 (53$^{rd}$ Ed., 1999).
*Physicians' Desk Reference* 3128 (53$^{rd}$ Ed., 1999).
*Physicians' Desk Reference for Nonprescription Drugs*, 718 (9th Ed., 1988).

* cited by examiner

*Primary Examiner*—Russell Travers
(74) *Attorney, Agent, or Firm*—Nath & Associates PLLC; Gary M. Nath

(57) ABSTRACT

Multi-vitamin and mineral supplements for administration to non-lactating women, which comprise specific regimens of vitamins and minerals tailored to meet the physiological needs of said women. Methods for optimizing the health of women by providing multi-vitamin and mineral supplements which are specifically tailored to achieve optimal regulation of growth, maintenance and repair of body tissue during specific stages of life with minimal side effects. Methods for formulating a multi-vitamin and mineral supplement that optimize the health of a woman and which comprise identifying life stages which correlate to specific nutritional requirements as a result of varying physiological conditions during a lifetime and selecting specific types and optimal amounts of vitamins and minerals for said life stages.

14 Claims, No Drawings

MULTI-VITAMIN AND MINERAL SUPPLEMENTS FOR WOMEN

RELATED APPLICATION

This application is a continuation of U.S. patent application No. 09/128,466, filed Aug. 4, 1998, now abandoned Continuation-in-Part application of U.S. patent application Ser. No. 08/474,071 filed Jun. 7, 1995, now issued U.S. Pat. No. 5,869,084, issued Feb. 9, 1999 which is a Continuation-in-Part application of U.S. patent application Ser. No. 08/262,515 filed Jun. 20, 1994, now abandoned the entire contents of which are incorporated herein in their entirety.

BACKGROUND OF THE INVENTION

1. Field of the Invention

The present invention relates to multi-vitamin and mineral supplements, and particularly to multi-vitamin and mineral supplements for administration to women. The go supplements are specifically tailored to meet nutritional requirements and maintain a woman s health during specific stages of life. The present invention also relates to methods of optimizing the health of women by providing multi-vitamin and mineral supplements which are specifically tailored to achieve optimal regulation of growth, maintenance and repair of body tissue during specific stages of life with minimal side effects. Methods of formulating multi-vitamin and mineral supplements for life stages are also encompassed by the present invention.

2. Description of Related Art

Vitamin and mineral preparations are commonly administered to treat specific medical conditions or as general nutritional supplements. Recent studies have elucidated the important physiological roles played by vitamins and minerals, and established a correlation between deficiencies or excesses of these nutrients and the etiologies of certain disease states in humans. See, e.g., Diplock, "Antioxidant Nutrients and Disease Prevention: An Overview," Am. J. Clin. Nutr., 53:189–193 (1991); Document Geigy Scientific Tables, 457–497 (Diem and Cemtuer eds., 7th ed., 1975).

It has further become recognized that various life-stage groups of the human population require different quantities; and types of vitamins and minerals to prevent or alleviate diseases, as well as to maintain general good health. For example, it is known that pregnant women commonly require iron therapy to prevent or treat iron-deficiency anemia.

Various prior patents have been directed to improving the efficacy of iron supplements for use during pregnancy.

U.S. Pat. No. 4,994,283, for example, discloses nutritional mineral supplements which include iron and calcium compounds in combination with citrates or tartrates, ascorbates, and fructose. The tendency of calcium to inhibit the bioavailability of iron is said to be reduced in such compositions, so that the conjoint bioavailability of these two minerals is enhanced.

U.S. Pat. No. 4,431,634 discloses maximization of iron bioavailability in prenatal iron supplements by maintaining the amount of calcium compounds in the supplement at 300 mg or less and the amount of magnesium compounds at 75 mg or less per dosage unit.

Another approach to the same problem is found in U.S. Pat. No. 4,752,479, wherein a multi-vitamin and mineral dietary supplement is provided which includes (a) one or more divalent dietary mineral components such as calcium or magnesium; and (b) a bioavailable iron component, presenting a controlled release form and adapted to be released in a controlled manner in the gastrointestinal tract.

U.S. Pat. No. 4,710,387 discloses a nutritional supplement preparation for pregnant and breast-feeding women which contains 10–20% by weight of protein, 16–28% by weight of fat, 43–65% by weight carbohydrates, and at most 3.5% by weight of moisture, minerals, trace elements and vitamins.

Multi-vitamin and mineral formulations which are directed specifically to woman have been disclosed in prior patents and in the medical literature.

The Physicians' Desk Reference (PDR) for Nonprescription Drugs, 9th Edition, 718–19 (1988) discloses a complete calcium/vitamin/mineral supplement program formulated for women. The program contains two specific formulas. One formulation is directed to woman between the ages of 14 and 40, and the other formulation is directed to woman over the age of 40. These formulations do not specifically distinguish between the varying physiological states experienced by women throughout the course of their lives. In fact, by providing one formulation for the broad category of woman aged 14–40, this disclosure highlights the need for more specific formulations.

The Handbook of Nonprescription Drugs, 9th Edition, 447–51, discloses amounts of vitamins and minerals which are optimum for pregnant and lactating women. However, no distinction is drawn between what amounts are optimum for pregnant versus lactating women. Further, there is no identification of specific amounts of vitamins and minerals correlating specifically to any other life stages of women. Moreover, the reference teaches that the prime criteria for optimum nutrition are age, weight, height and sex.

WO 95/35098 discloses multi-vitamin and mineral supplements for administration to lactating, non-lactating, and menopausal women which comprise specific regimens of critical nutritional agents. This reference teaches formulations containing high amounts of iron, zinc and vitamin $B_{12}$, and low amounts of vitamin $B_{12}$ and vitamin $B_6$.

Despite the foregoing efforts to improve vitamin and mineral supplementation for pregnant women, conventional prenatal supplements are not ideally suited for women during other phases of their lives. Moreover, the foregoing efforts to improve vitamin and mineral supplementation for women, in general, have lacked the specificity required for achieving formulations which are truly adapted to meet the physiological needs of woman at various times in their lives. For example, the nutritional needs of lactating women following a pregnancy differ from the nutritional needs of women during pregnancy. The vitamin and mineral requirements for non-lactating and menopausal women also differ from the requirements of pregnant women.

Conventional nutritional formulations are poorly designed for administration to women during various stages of life in which the physiological requirements of the women vary significantly. As such, the previously disclosed multi-vitamin and mineral formulations do not truly meet the specific needs of women. It would therefore be desirable to provide multi-vitamin and mineral supplements which obviate the deficiencies of known vitamin and mineral products while satisfying the long standing need for such supplements.

None of the above described references is admitted to be prior art.

SUMMARY OF THE INVENTION

The present invention overcomes the shortcomings of known nutritional supplements by providing multivitamin and mineral supplements which are specifically tailored for administration to woman during various stages of life, and more specifically to lactating, non-lactating, and menopausal women. The formulations of the invention have been found to maximize the benefits of vitamin and mineral supplementation for women by specifically formulating the products to meet the physiological requirements of women during these life stages.

Moreover, the bioavailability of each vitamin and mineral in a multi-vitamin formulation is affected by the presence of other vitamins and minerals in the formulation, as well as by the amounts of each vitamin and mineral present and the physiological state of the individual using said formulation. Use of the specific formulations of the present invention for the prescribed life stages unexpectedly results in a higher bioavailability of essential nutrients.

The compositions of the invention include certain essential nutritional components in dosage levels which have been found to optimize the maintenance of a woman's health during each of the noted stages of life. Minerals such as calcium, zinc and iron are dosed (i.e. provided in the supplement) in the form of a corresponding pharmaceutically acceptable compound.

According to a first aspect of the invention, a multi-vitamin and mineral supplement for administration to a lactating woman is provided. This supplement is specially designed to aid in fulfilling the dietary needs of women who are producing and secreting milk, that is, lactating women. The multi-vitamin and mineral supplement comprises:

(a) from about 350 mg to about 480 mg of elemental calcium dosed in the form of a pharmaceutically acceptable calcium compound;
(b) from about 400 I.U. to about 600 I.U. of vitamin D;
(c) from about 400 I.U. to about 8,000 I.U. of Beta carotene, or about 3600 I.U. to about 10,000 I.U. of vitamin A or mixtures thereof;
(d) from about 9.6 mcg to about 14.4 mcg of vitamin B12;
(e) from about 8 mg to about 12 mg of vitamin B6;
(f) from about 15 mg to about 30 mg of vitamin B3;
(g) from about 45 mg to about 4.0 mg of vitamin B2;
(h) from about 3.2 mg to about 4.6 mg of vitamin B1;
(i) from about 24 I.U. to about 36 I.U. of vitamin E;
(j) from about 10 mg to about 30 mg of elemental iron, dosed in the form of a pharmaceutically acceptable iron compound; and
(k) from about 20 mg to about 30 mg of elemental zinc, dosed in the form of a pharmaceutically acceptable zinc compound.

A multi-vitamin and mineral supplement for administration to a non-lactating woman is also provided by the invention. This supplement is designed to aid in fulfilling the dietary needs of women during the period after puberty and before menopause who are neither pregnant nor lactating. This formulation comprises:

(a) a total daily dosage of about 160 mg to about 240 mg of elemental calcium dosed in the form of a pharmaceutically acceptable calcium compound;
(b) a total daily dosage of about 320 I.U. to about 480 I.U. of vitamin D;
(c) a total daily dosage of about 2,000 I.U. to about 6,000 I.U. of vitamin A or mixtures thereof;
(d) a total daily dosage of about 0.006 mg to about 0.040 mg of vitamin $B_{12}$;
(e) a total daily dosage of about 8 mg to about 26 mg of vitamin $B_6$;
(f) a total daily dosage of about 10 mg to about 30 mg of vitamin $B_3$;
(g) a total daily dosage of about 2.5 mg to about 4.0 mg of vitamin $B_2$;
(h) a total daily dosage of about 2.6 mg to about 4.8 mg of vitamin $B_1$;
(i) a total daily dosage of about 24 I.U. to about 100 I.U. of vitamin E;
(j) a total daily dosage of about 6 mg to about 42 mg of elemental iron dosed in the form of a pharmaceutically acceptable iron compound; and
(k) a total daily dosage of about 12 mg to about 30 mg of elemental zinc dosed in the form of a pharmaceutically acceptable zinc compound.

A multi-vitamin and mineral supplement for administration to a menopausal woman is also provided. This supplement is specially designed to aid in fulfilling the dietary needs of women during the transitional period marked by the cessation of menses. Menopausal women may be asymptomatic or experience a variety of symptoms including hot flushes. See The Merck Manual of Diagnosis and Therapy 15th edition, 1713–1715. Most menopausal women experience hot flushes for over a year and 25 to 50% experience hot flushes for more than five years. The supplement for menopausal women of the present invention comprises:

(a) from about 320 mg to about 480 mg of elemental calcium dosed in the form of a pharmaceutically acceptable calcium compound;
(b) from about 320 I.U. to about 480 I.U. of vitamin D;
(c) from about 250 I.U. to about 5000 I.U. of Beta-carotene, or from about 2,000 I.U. to 6,000 I.U. of vitamin A and mixtures thereof;
(d) from about 20 mcg to about 30 mcg of vitamin B12;
(e) from about 2.4 mg to about 3.6 mg of vitamin B6;
(f) from about 16 mcg to about 24 mg of vitamin B3;
(g) from about 1.3 mg to about 2.0 mg of vitamin B2;
(h) from about 1.2 mg to about 2.8 mg of vitamin B1;
(i) from about 7 mg to about 11 mg of elemental iron dosed in the form of a pharmaceutically acceptable iron compound;
(k) from about 16 mg to about 24 mg of elemental zinc dosed in the form of a pharmaceutically acceptable zinc compound;
(l) from about 40 mcg to about 60 mcg of elemental molybdenum in the form of a pharmaceutically acceptable molybdenum compound;
(m) from about 80 mcg to about 120 mcg of elemental chromium dosed in the form of a pharmaceutically acceptable chromium compound.

A method for optimizing the health of a woman is also included in the present invention. The method comprises administering to said woman a multi-vitamin and mineral supplement comprising vitamins and minerals in amounts adjusted according to varying physiological conditions of said woman over a lifetime.

A method for formulating a multi-vitamin and mineral supplement which optimizes the health of a woman is also provided. This method comprises:

(a) identifying a life stage of a woman which presents specific nutritional requirements as a result of varying physiological conditions over a lifetime;
(b) selecting specific vitamins and minerals according to the varying physiological conditions;
(c) determining optimal amounts of each vitamin and mineral according to varying physiological conditions of said woman over a lifetime; and (d) preparing a multi-vitamin and mineral supplement containing the determined optimal amounts of each vitamin and mineral of step (c).

Thus, the invention provides the above-described multi-vitamin and mineral supplements for administration to lactating, non-lactating, and menopausal women, as well as methods both for optimizing the health of women and for preparing formulations for same. In contrast to conventional vitamin and mineral products, the formulations of the invention comprise specific regimens of critical nutritional agents, in order to better meet the physiological requirements of women and maintain good health throughout life.

DESCRIPTION OF THE PREFERRED EMBODIMENTS

As used herein, "non-lactating woman" refers to a woman who has experienced puberty, but has not experienced menopause, and who is not lactating and not pregnant.

"Nutrient" refers to any substance in a human or other living organism which regulates the growth, maintenance, and repair of body tissue, as well as any substance which provides energy or structural material to the body.

"Essential nutrient" refers to any nutrient which is not produced by a human or other living organism and thus must be obtained from an external source.

"Body tissue", refers to any substance in a human or other living organism which is composed of the cells of said human or other organism, respectively.

"Total daily dosage" refers to the amount of any nutrient formulated for administration during any 24 hour period of time.

"AM dose" refers to any dose of a multi-vitamin and mineral supplement formulated for administration in the morning hours, and likewise, "PM dose" refers to any dose of a multi-vitamin and mineral supplement formulated for administration in the afternoon, evening or nighttime hours.

"Life stage" refers to a specific period of time during the course of an individual's life.

The invention provides multi-vitamin and mineral supplements which are tailored for women at different life stages, and specifically for administration to lactating, non-lactating, and menopausal women. The formulations of the invention include certain essential nutritional components in dosage levels which have been found to optimize the maintenance of a woman's health during each of these stages of life.

According to a first aspect of the invention, a multi-vitamin and mineral supplement for administration to a lactating woman is provided, which comprises:

(a) from about 320 mg to about 480 mg of elemental calcium dosed in the form of a pharmaceutically acceptable calcium compound;

(b) from about 400 I.U. to about 600 I.U. of vitamin D;

(c) from about 400 I.U. to about 8000 I.U. of Beta-carotene, or about 3600 I.U. to about 10,000 I.U. of vitamin A or mixtures thereof;

(d) from about 9.6 mcg to about 14.4 mcg of vitamin B12;

(e) from about 8 mg to about 12 mg of vitamin B6;

(f) from about 15 mg to about 30 mg of vitamin B3;

(g) from about 2.7 mg to about 4 mg of vitamin B2;

(h) from 3.2 mg to about 4.8 mg of vitamin B1;

(i) from about 24 I.U. to about 36 I.U. of vitamin E;

(j) from about 10 mg to about 30 mg of elemental iron dosed in the form of a pharmaceutically acceptable iron compound; and (k) from about 20 mg to about 30 mg of elemental SE zinc dosed in the form of a pharmaceutically acceptable zinc compound.

A particularly preferred multi-vitamin and mineral supplement for lactating women also includes from about 160 mg to about 240 mg of a pharmaceutically acceptable magnesium compound and about 95 mg to about 145 mg of vitamin C.

A multi-vitamin and mineral supplement for administration to a non-lactating woman is also provided by the invention. This supplement is designed to specifically aid in fulfilling the dietary needs of women during the period after puberty and before menopause who are neither pregnant nor lactating. The invention may be used by a non-lactating woman who has never given birth or a non-lactating woman who has given birth one or more times. The formulation comprises:

(a) a total daily dosage of about 160 mg to about 240 mg of elemental calcium dosed in the form of a pharmaceutically acceptable calcium compound;

(b) a total daily dosage of about 320 I.U. to about 480 I.U. of vitamin D;

(c) a total daily dosage of about 2,000 I.U. to about 5,400 I.U. of vitamin A or mixtures thereof;

(d) a total daily dosage of about 0.006 mg to about 0.040 mg of vitamin $B_{12}$;

(e) a total daily dosage of about 8 mg to about 26 mg of vitamin $B_6$;

(f) a total daily dosage of about 15 mg to about 30 mg of vitamin $B_3$;

(g) a total daily dosage of about 2.7 mg to about 4.0 mg of vitamin $B_2$;

(h) a total daily dosage of about 2.6 mg to about 4.8 mg of vitamin $B_1$;

(i) a total daily dosage of about 24 I.U. to about 100 I.U. of vitamin E;

(j) a total daily dosage of about 10 mg to about 30 mg of elemental iron dosed in the form of a pharmaceutically acceptable iron compound; and (k) a total daily dosage of about 12 mg to about 30 mg of elemental zinc dosed in the form of a pharmaceutically acceptable zinc compound.

Preferably, the multi-vitamin and mineral supplement for non-lactating women also includes from about 160 mg to about 240 mg of a pharmaceutically acceptable magnesium compound and about 95 mg to about 300 mg of vitamin C, or more preferably from about 180 mg to about 220 mg of a pharmaceutically acceptable magnesium compound, from about 180 mg to about 220 mg of vitamin C, from about 0.040 mg to about 0.060 mg of a pharmaceutically acceptable molybdenum compound, and from about 0.080 mg to about 0.120 mg of a pharmaceutically acceptable chromium compound.

Even more preferably, the present invention includes a multi-vitamin and mineral supplement for administration to a non-lactating woman which comprises:

(a) a total daily dosage of about 180 mg to about 220 mg of elemental calcium dosed in the form of a pharmaceutically acceptable calcium compound;

(b) a total daily dosage of about 380 I.U. to about 420 I.U. of vitamin D;

(c) a total daily dosage of about 4,500 I.U. to about 5,500 I.U. of vitamin A or mixtures thereof;

(d) a total daily dosage of about 0.010 mg to about 0.030 mg of vitamin $B_{,2}$;

(e) a total daily dosage of about 16 mg to about 24 mg of vitamin $B_6$;
(f) a total daily dosage of about 17 mg to about 25 mg of vitamin $B_3$;
(g) a total daily dosage of about 3.0 mg to about 3.8 mg of vitamin $B_2$;
(h) a total daily dosage of about 2.7 mg to about 3.5 mg of vitamin $B_2$;
(i) a total daily dosage of about 64 I.U. to about 95 I.U. of vitamin E;
(j) a total daily dosage of about 10 mg to about 30 mg of elemental iron dosed in the form of a pharmaceutically acceptable iron compound; and
(k) a total daily dosage of about 14 mg to about 25 mg of elemental zinc dosed in the form of a pharmaceutically acceptable zinc compound.

Most preferably, the present invention includes a multi-vitamin and mineral supplement for administration to a non-lactating woman which comprises:
(a) a total daily dosage of about 190 mg to about 210 mg of elemental calcium dosed in the form of a pharmaceutically acceptable calcium compound;
(b) a total daily dosage of about 395 I.U. to about 405 I.U. of vitamin D;
(c) a total daily dosage of about 4,750 I.U. to about 5,250 I.U. of vitamin A or mixtures thereof;
(d) a total daily dosage of about 0.016 mg to about 0.024 mg of vitamin $B_{12}$;
(e) a total daily dosage of about 18 mg to about 22 mg of vitamin $B_6$;
(f) a total daily dosage of about 18 mg to about 22 mg of vitamin $B_3$;
(g) a total daily dosage of about 3.2 mg to about 3.6 mg of vitamin $B_2$;
(h) a total daily dosage of about 2.8 mg to about 3.2 mg of vitamin $B_1$;
(i) a total daily dosage of about 70 I.U. to about 80 I.U. of vitamin E;
(j) a total daily dosage of about 15 mg to about 24 mg of elemental iron dosed in the form of a pharmaceutically acceptable iron compound; and
(k) a total daily dosage of about 14 mg to about 25 mg of elemental zinc dosed in the form of a pharmaceutically acceptable zinc compound.

A multi-vitamin and mineral supplement for administration to a menopausal woman is also provided, which comprises:
(a) from about 320 mg to about 480 mg of elemental calcium dosed in the form of a pharmaceutically acceptable calcium compound;
(b) from about 320 I.U. to about 480 I.U. of vitamin D;
(c) from about 250 I.U. to about 750 I.U. of Beta-carotene or from about 3,600 I.U. to about 5,400 I.U. of vitamin A and mixtures thereof;
(d) from about 20 mcg to about 30 mcg of vitamin B12;
(e) from about 2.4 mg to about 3.6 mg of vitamin B6;
(f) from about 16 mg to about 24 mg of vitamin B3;
(g) from about 1.3 mg to about 2.0 mg of vitamin B2;
(h) from about 1.2 mg to about 1.8 mg of vitamin B1;
(i) from about 70 I.U. to about 110 I.U. of vitamin E;
(j) from about 7 mg to about 11 mg of elemental iron dosed in the form of a pharmaceutically acceptable iron compound;
(k) from about 16 mg to about 24 mg of elemental zinc dosed in the form of a pharmaceutically acceptable zinc compound;
(l) from about 40 mcg to about 60 mcg of element molybdenum dosed in the form of a pharmaceutically acceptable molybdenum compound; and
(m) from about 80 mcg to about 120 mcg of elemental chromium dosed in the form of a pharmaceutically acceptable chromium compound.

A particularly preferred multi-vitamin and mineral supplement for menopausal women also includes about 160 mg to about 240 mg of a pharmaceutically acceptable magnesium compound.

A method for optimizing the health of a woman is also provided in the present invention. The method comprises administering to said woman a multi-vitamin and mineral supplement comprising vitamins and minerals in amounts adjusted according to varying physiological conditions of said woman over a lifetime.

Preferably, the method comprises administering to said non-lactating woman a multi-vitamin and mineral supplement comprising:
(a) a total daily dosage of about 160 mg to about 240 mg of elemental calcium dosed in the form of a pharmaceutically acceptable calcium compound;
(b) a total daily dosage of about 320 I.U. to about 480 I.U. of vitamin D;
(c) a total daily dosage of about 2,000 I.U. to about 5,400 I.U. of vitamin A or mixtures thereof;
(d) a total daily dosage of about 0.006 mg to about 0.040 mg of vitamin $B_{12}$;
(e) a total daily dosage of about 8 mg to about 26 mg of vitamin $B_6$;
(f) a total daily dosage of about 20 mg to about 30 mg of vitamin $B_3$;
(g) a total daily dosage of about 2.7 mg to about 4.0 mg of vitamin $B_2$;
(h) a total daily dosage of about 2.6 mg to about 4.8 mg of vitamin $B_1$;
(i) a total daily dosage of about 24 I.U. to about 100 I.U. of vitamin E;
(j) a total daily dosage of about 6 mg to about 42 mg of elemental iron dosed in the form of a pharmaceutically acceptable iron compound; and
(k) a total daily dosage of about 12 mg to about 30 mg of elemental zinc dosed in the form of a pharmaceutically acceptable zinc compound.

A method for formulating a multi-vitamin and mineral supplement which optimizes the health of a woman is also included. This method comprises:
(a) identifying a life stage of a woman which presents specific nutritional requirements as a result of varying physiological conditions over a lifetime;
(b) selecting specific vitamins and minerals according to the varying physiological conditions;
(c) determining optimal amounts of each vitamin and mineral according to the varying physiological conditions of said woman over a lifetime; and
(d) preparing a multi-vitamin and mineral supplement containing the determined optimal amounts of each vitamin and mineral of step (c).

It will be noted that the formulations vary in the critical nutritional agents included and amounts thereof. For example, because calcium is essential for the production of milk, levels of calcium are higher for administration to lactating women than in the non-lactating and menopausal formulations. As menopausal women do not lose iron like women with menstrual cycles, the amount of iron in the menopausal formulation is reduced greatly in comparison to the formulations for lactating and non-lactating women. Molybdenum and chromium are added to the menopausal formulation because these agents are believed to assist the immune system, which is a useful therapy in older women.

Various side effects may be associated with the use of certain vitamins and minerals at various times in some individuals. For example, women who are pregnant and experiencing morning sickness can not tolerate excessive levels of iron. However, women who are not pregnant are able to tolerate higher levels of iron and it may be advantageous for them to take a formulation with more iron. Other side effects are experienced when using niacin, magnesium and other such vitamins and minerals, without limitation. By recognizing the correlation between different life stages of women and the amount of each vitamin and mineral which may induce side effects, the present invention addresses the problem of providing optimal supplementation of vitamins and minerals while eliminating or at least minimizing said side effects. Accordingly, the present invention is designed to minimize adverse effects often experienced by women when taking vitamin and mineral supplements while providing the optimal amount of vitamins and minerals.

The present invention is contemplated for use by women of varying physical conditions, without limitation, including normal, healthy women and women with a physical disorder, vitamin or mineral deficiency, or a nutritional disorder. Non-limiting exemplary vitamin deficiencies include vitamin A deficiency, hypervitaminosis A, vitamin D deficiency and dependency, hypervitaminosis D, vitamin E deficiency and toxicity, vitamin K deficiency, hypervitaminosis K, essential fatty acid deficiency, thiamine deficiency, riboflavin deficiency, niacin deficiency, vitamin $B_6$ deficiency and dependency, biotin deficiency and dependancy, pantothenic acid deficiency, carnitine deficiency and vitamin C deficiency. Non-limiting exemplary mineral deficiencies include phosphate depletion, iodine deficiency, fluorine deficiency, zinc deficiency disturbances in copper metabolism, acquired copper deficiency, acquired copper toxicosis, inherited copper deficiency and inherited copper toxicosis.

Useful pharmaceutically acceptable calcium compounds include, without limitation, any of the well-known calcium supplements such as calcium carbonate, calcium phosphate, calcium citrate, calcium sulfate, calcium oxide, calcium hydroxide, calcium apatite, calcium citrate-maleate, calcium lactate, calcium levulinate and the like. Preferably, calcium compounds selected from the group consisting of calcium carbonate, calcium sulfate, and mixtures thereof are employed.

Useful pharmaceutically acceptable zinc compounds include, without limitation, zinc sulfate, zinc chloride, and zinc oxide, with zinc sulfate being preferred.

The pharmaceutically acceptable iron compound may be chosen from any of the well-known iron II (ferrous) or iron III (ferric) supplements, such as ferrous fumarate, ferrous sulfate, carbonyl iron, ferrous glucomate, ferrous chloride, ferrous lactate, ferrous tartrate, ferrous succinate, ferrous glutamate, ferrous citrate, ferrous pyrophosphate, ferrous cholinisocitrate, ferrous carbonate, iron-sugarcarboxylate complexes and the like, without limitation.

Preferably, the iron compound comprises a pharmaceutically acceptable iron compound contained in a pharmaceutically acceptable film forming material which permits release of the iron in the stomach of a woman administered the supplement. The iron may or may not be coated. Suitable coatings include, without limitation, any material known in the art for forming enteric, controlled release, or sustained release coatings, such as cellulose ethers including hydroxypropyl methylcellulose, methylcellulose, ethylcellulose, and carboxymethylcellulose; cellulose esters such as cellulose acetate, cellulose acetate phthalate, and cellulose nitrate; acrylate and methacrylate copolymers; and the like. The coated iron compound has been found to provide increased iron bioavailability by minimizing interaction between the iron compound and divalent cations such as calcium in the nutritional supplement. Release of the iron in the intestine also minimizes stomach upset. More preferably, the iron is in the coating and is released in the stomach.

It is also possible in the present formulations to combine various forms of extended release particles or coatings along with immediate release particles or coatings to deliver the various vitamins and mineral supplements over various rates of release, without limitation. For example, certain agents such as thiamine, niacinamide, pyridoxine, ascorbic acid, folic acid, iron and riboflavin could be released over an extended period of time from two hours up to 24 hours while other agents such as beta-carotene, vitamin A, vitamin $D_3$, vitamin $B_{12}$, biotin, pantothenic acid, copper, zinc, magnesium, potassium, iodine, chromium, molybdenum and selenium can be administered as immediate release. The ability to obtain extended and immediate release characteristics is performed using well known procedures and techniques available to the ordinary skilled artisan.

The multi-vitamin and mineral supplements of the invention may include additional nutritional components well-known in the art. For example, the supplements may include elemental magnesium dosed in the form of one or more pharmaceutically acceptable magnesium compounds, without limitation, such as magnesium stearate, magnesium carbonate, magnesium oxide, magnesium hydroxide, and magnesium sulfate. Magnesium stearate is a preferred form of the compound. The formulations may also include vitamin C, from about 0.1 mg to about 1 mg of folic acid, from 1 mg to about 3 mg of copper, and from about 0.05 mg to about 0.25 mg of iodine. Other nutritional agents well-known in the art may be included as desired.

In a preferred embodiment of the formulations, the optional vitamin C and folic acid nutritional components are coated to provide controlled release of these agents. The techniques and materials discussed above that are utilized to coat iron are preferred.

Pharmaceutically acceptable copper compounds include, without limitation, cupric oxide, cupric sulfate, or cupric gluconate, with cupric oxide being preferred. Preferred pharmaceutically acceptable iodine compounds include sodium or potassium iodide, with potassium iodide being most preferred.

The vitamins in the formulation may be provided in any source, without limitation. The amounts shown for each vitamin and mineral indicate the actual vitamin and mineral amounts, in milligrams (mg), in the formulations regardless of source, except where otherwise indicated. Vitamin A may be provided in any source, such as a preformed vitamin A compound or a vitamin A precursor, or any combination thereof. The amount of vitamin A in the formulations is expressed as an International Unit (I.U.) which is a measure of vitamin activity. Therefore, the indicated amounts for vitamin A refer to any amount of any precursor or preformed vitamin A compound, from any source whatsoever, which would result in the indicated amount of vitamin A activity in the body. The ability to determine such amounts and achieve formulations containing same is performed using well known procedures and techniques available to the ordinary skilled artisan.

The nutritional supplements of the invention may be provided in any suitable dosage form known in the art, without limitation. For example, the compositions may be incorporated into tablets, powders, granules, beads, chewable lozenges, capsules, liquids, or similar conventional dosage forms, using conventional equipment and techniques known in the art. Tablet dosage forms are preferred.

Furthermore, the dosage form can be in the form of a bi-layer tablet composed of at least one extended-release layer and at least one immediaterelease layer. Also, the bi-layer tablet can be coated for ease of administration or can be enteric coated to reduce any gastric irritation and the unpleasant "burping" produced by the vitamins and minerals. Also, multi-particulate design of extended release and immediate-release components can be enteric coated and compressed into a tablet or filled into hard or soft gelatin capsules.

When preparing dosage forms incorporating the compositions of the invention, the nutritional components are normally blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethyl cellulose and sodium starch glycolate; suspending agents, such as povidone, polyvinyl alcohol and the like; absorbent, such as silicon dioxide; preservatives, such as methylparaben, propylparaben, and sodium benzoate; surfactants, such as sodium lauryl sulfate, polysorbate 80, and the like; and colorants, such as F.D. & C dyes and lakes.

For preparing compositions from the compounds described by this invention, inert, pharmaceutically acceptable carriers can be used which are either solid or liquid. Solid form preparations include powders, tablets, dispersible granules, capsules, and cachets. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compounds. In the tablet the active compound is mixed with carrier having the necessary binding properties in suitable proportions and compacted in the shape and size desired. The powders and tablets preferably contain from 5 or 10 to about 90 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, coca butter, and the like. The term "preparation" is intended to include the formulation of the active compounds with encapsulating material as carrier providing a capsule in which the active component (with or without other carriers) is surrounded by carrier, which is thus in association with it. Similarly, cachets are included. Tablets, powders, cachets, and capsules can be used a solid dosage forms suitable for oral administration. Liquid form preparations include solutions, suspensions, and emulsions. As an example, water or water/propylene glycol solutions for parenteral injection may be used. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition.

The solid and liquid forms may contain, in addition to the active addition to the material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the preparations are in unit dosage form. In such form, the preparation is subdivided into unit doses containing appropriate quantities of the active components. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied according to the particular application and the potency of the active ingredients.

Determination of the proper dosage for a particular situation is well within the skill of the art. For convenience, the total daily dosage may be divided and administered in portions during the day if desired or at one time, morning, afternoon, or night as well as biphasic, triphasic, etc. Moreover, the portion administered in one dose during a day need not be equal to all or any other doses administered during a day.

For example, if the total daily dosage is divided into two different doses, such as an AM and a PM dose, then one vitamin, such as vitamin $B_6$, may be present in a lesser amount in the AM dose than in the PM dose. Several or all of the vitamins and/or minerals may be treated in such a manner. The amount of a vitamin and mineral in each dose is determined as the amount which will achieve optimal or maximal efficacy with minimal side effects. The use of such unequal doses during the course of a day may apply to the entire formulation, or any individual vitamin or mineral in said formulation. Moreover, it is believed that the use of unequal doses increases the bioavailability of some or all of the nutrients provided in the formulations.

Controlled and uncontrolled release formulations, as well as sustained release, extended release, timed release, delayed release and other such formulations, without limitation, are contemplated for use with the present invention.

Although the products of the invention are preferably intended for administration to humans, it will be understood that the formulation may also be utilized in veterinary therapies for other animals.

The following examples are given to illustrate the invention but are not deemed to be limiting thereof. All amounts specified in the application are based on milligrams (mg) unless otherwise indicated. The term ".I.U." represents International Units.

EXAMPLE 1

Preparation of Multi-Vitamin and Mineral Supplements

The following compositions were used to prepare multi-vitamin and mineral supplements for administration to lactating, non-lactating, and menopausal women:

TABLE I

| Component | Lactating | Non-Lactating | Menopausal |
| --- | --- | --- | --- |
| Calcium, mg | 320–480 | 160–240 | 320–480 |
| Vitamin D, I.U. | 400–600 | 320–480 | 320–480 |
| Vitamin B12, mg | 0.006–0.015 | 0.006–0.040 | 0.020–0.030 |
| Vitamin B6, mg | 8–40 | 8–40 | 8–40 |
| Vitamin B3, mg | 18–30 | 15–30 | 10–40 |
| Vitamin B2, mg | 2.7–5.0 | 2.7–5.0 | 2.7–5.0 |
| Vitamin B1, mg | 3.2–4.8 | 2.6–4.8 | 1–3 |
| Vitamin E, I.U. | 20–40 | 24–100 | 70–110 |
| Iron, mg | 28–43 | 6–42 | 7–11 |
| Zinc, mg | 20–30 | 12–30 | 10–30 |
| Vitamin C, mg | 60–300 | 60–300 | 60–300 |
| Molybdenum, mg | 0.020–0.030 | 0.040–0.060 | 0.040–0.060 |
| Chromium, mg | 0.040–0.060 | 0.080–0.120 | 0.080–0.120 |
| Vitamin A, I.U. | 2,000–10,000 | 2,000–10,000 | 2,000–10,000 |
| Potassium, mg. | 40–60 | 40–60 | 64–96 |
| Pantothenic Acid, mg | 12–18 | 8–12 | 8–12 |
| Folic Acid, mg | 0.8–1.2 | 0.8–1.2 | 0.8–1.2 |
| Biotin, mcg | 0.040–0.060 | 0.240–0.360 | 0.240–0.360 |
| Copper, mg | 1.6–2.4 | 1.6–2.4 | 1.6–2.4 |
| Iodine, mg | 0.120–.180 | 0.120–0.180 | 0.120–0.180 |
| Magnesium, mg | 160–240 | 160–240 | 160–240 |

Tablets incorporating the above formulations were prepared using conventional methods and materials known in the pharmaceutical art. The resulting nutritional supplement tablets were recovered and stored for future use.

EXAMPLE 2

The following compositions were used to prepare multi-vitamin and mineral supplements for administration to lactating, non-lactating and menopausal women.

TABLE II

| Component | Lactating | Non-Lactating | Menopausal |
| --- | --- | --- | --- |
| Calcium, mg | 400 | 200 | 400 |
| Vitamin D, I.U. | 500 | 400 | 400 |
| Vitamin B12, mg | 0.012 | 0.020 | .025 |
| Vitamin B6, mg | 10 | 20 | 3 |
| Vitamin B3, mg | 25 | 20 | 20 |
| Vitamin B2, mg | 3.4 | 3.4 | 1.7 |
| Vitamin B1, mg | 4.0 | 3.0 | 1.5 |
| Vitamin E, I.U. | 30 | 75 | 90 |
| Iron, mg | 36 | 18 | 9 |
| Zinc, mg | 25 | 15 | 20 |
| Vitamin C, mg | 120 | 200 | 240 |
| Potassium, mg | — | 25 | 80 |
| Pantothenic Acid, mg | 15 | 10 | 10 |

TABLE II-continued

| Component | Lactating | Non-Lactating | Menopausal |
| --- | --- | --- | --- |
| Folic Acid, mg | 1.0 | 1.0 | 0.5 |
| Biotin, mg | 0.050 | 0.03 | 0.300 |
| Copper, mg | 2 | 2 | 2 |
| Iodide, mg | 0.150 | 0.150 | 0.150 |
| Magnesium, mg | 200 | 200 | 200 |

The invention being thus described, it will be apparent that the same may be varied in many ways. Such variations are not to be regarded as a departure from the spirit and scope of the invention, and all such modifications are intended to be within the scope of the appended claim.

We claim:

1. A method for providing multi-vitamin and mineral supplementation to a lactating woman which comprises:

administering to said lactating woman a multi-vitamin and mineral supplement, comprising:
   (a) a total daily dosage of about 0.006 mg to about 0.040 mg of vitamin $B_{12}$;
   (b) a total daily dosage of about 8 mg to about 40 mg of vitamin $B_6$;
   (c) a total daily dosage of about 18 mg to about 30 mg of vitamin $B_3$;
   (d) a total daily dosage of about 2.7 mg to about 5.0 mg of vitamin $B_2$;
   (e) a total daily dosage of about 28 mg to about 68 mg of elemental iron dosed in the form of a pharmaceutically acceptable iron compound; and
   (f) a total daily dosage of about 20 mg to about 30 mg of elemental zinc dosed in the form of a pharmaceutically acceptable zinc compound.

2. The method of claim 1, further comprising a total daily dosage of about 250 I.U. to about 750 I.U. of beta carotene or about 3,600 I.U. to about 5,400 I.U. of vitamin A or mixtures thereof.

3. The method of claim 1, wherein the total daily dosage of at least one vitamin or mineral is divided and administered in portions during the day.

4. The method of claimed 1, wherein the total daily dosage of at least one vitamin or mineral is divided and administered in uneven portions during the day.

5. The method of claim 1, wherein the multi-vitamin and mineral supplement is administered to meet nutritional requirements of a lactating woman while avoiding inducement of side effects.

6. A method for providing multi-vitamin and mineral supplementation to a non-lactating woman, which comprises:

administering to said lactating woman a multi-vitamin and mineral supplement, comprising:
   (a) a total daily dosage of about 0.006 mg to about 0.040 mg of vitamin $B_{12}$;
   (b) a total daily dosage of about 8 mg to about 40 mg of vitamin $B_6$;
   (c) a total daily dosage of about 15 mg to about 30 mg of vitamin $B_3$;
   (d) a total daily dosage of about 2.7 mg to about 5.0 mg of vitamin $B_2$;
   (e) a total daily dosage of about 6 mg to about 42 mg of elemental iron dosed in the form of a pharmaceutically acceptable iron compound; and
   (g) a total daily dosage of about 12 mg to about 30 mg of elemental zinc dosed in the form of a pharmaceutically acceptable zinc compound.

7. The method of claim 6, further comprising a total daily dosage of about 60 mg to about 300 mg of vitamin C.

8. The method of claim 6, further comprising a total daily dosage of about 250 I.U. to about 750 I.U. of beta carotene or about 3,600 I.U. to about 5,400 I.U. of vitamin A or mixtures thereof.

9. The method of claim 6, wherein the total daily dosage of at least one vitamin or mineral is divided and administered in portions during the day.

10. The method of claim 6, wherein the total daily dosage of at least one vitamin or mineral is divided and administered in uneven portions during the day.

11. A method for providing multi-vitamin and mineral supplemenation to a menopausal woman, which comprises:

administering to said lactating woman a multi-vitamin and mineral supplement, comprising:
   - (a) a total daily dosage of about 8 mg to about 130 mg of vitamin $B_6$;
   - (b) a total daily dosage of about 10 mg to about 40 mg of vitamin $B_3$;
   - (c) a total daily dosage of about 2.7 mg to about 40 mg of vitamin $B_2$;
   - (d) a total daily dosage of about 6 mg to about 42 mg of elemental iron dosed in the form of a pharmaceutically acceptable iron compound; and
   - (e) a total daily dosage of about 10 mg to about 30 mg of elemental zinc dosed in the form of a pharmaceutically acceptable zinc compound.

12. The method of claim 11, further comprising a total daily dosage of about 60 mg to about 300 mg of vitamin C.

13. The method of claim 11, wherein the total daily dosage of at least one vitamin or mineral is divided and administered in portions during the day.

14. The method of claim 11, wherein the total daily dosage of at least one vitamin or mineral is divided and administered in uneven portions during the day.

* * * * *

UNITED STATES PATENT AND TRADEMARK OFFICE
CERTIFICATE OF CORRECTION

PATENT NO.     : 6,488,956 B1
DATED          : December 3, 2002
INVENTOR(S)    : George N. Paradissis et al.

It is certified that error appears in the above-identified patent and that said Letters Patent is hereby corrected as shown below:

<u>Title page,</u>
Item [75], Address on Inventor "Cuca", please replace "Edwardsville" with
-- Glen Carbon --.
Address on Inventor "Vanek", please replace "MO" with -- MD --.

Signed and Sealed this

First Day of April, 2003

JAMES E. ROGAN
*Director of the United States Patent and Trademark Office*